United States Patent [19]

Hammar

[11] Patent Number: 4,578,504
[45] Date of Patent: Mar. 25, 1986

[54] ACRYLATE AND METHACRYLATE MONOMERS AND POLYMERS

[75] Inventor: W. James Hammar, St. Paul, Minn.

[73] Assignee: Minnesota Mining and Manufacturing Company, St. Paul, Minn.

[21] Appl. No.: 500,782

[22] Filed: Jun. 3, 1983

[51] Int. Cl.$^4$ .................. C07C 69/78; C07C 69/653; C07C 143/68; C07F 7/08
[52] U.S. Cl. ........................ 560/112; 560/111; 560/223; 560/224; 556/428; 556/437; 558/52
[58] Field of Search ............... 260/456 F; 560/223, 560/224, 111, 112; 556/428, 437

[56] References Cited

U.S. PATENT DOCUMENTS

| | | | |
|---|---|---|---|
| 2,567,842 | 9/1951 | Erickson | 560/223 |
| 3,459,722 | 8/1969 | Zanger | 428/393 |
| 3,470,124 | 9/1969 | Eygen et al. | 524/544 |
| 3,501,448 | 3/1970 | Pittman et al. | 560/223 |
| 3,595,944 | 7/1971 | Manning et al. | 525/57 |
| 4,024,296 | 5/1977 | Gruber | 204/159.23 |
| 4,139,548 | 2/1979 | Tanaka et al. | 556/437 |
| 4,192,685 | 3/1980 | Horike et al. | 430/283 |

FOREIGN PATENT DOCUMENTS 1118007  6/1965  United Kingdom .

OTHER PUBLICATIONS

Kimura, Tadashi et al., Chemical Abstracts, vol. 79 (1973) #32, 383z.
Chemical Abstracts Service, Registry Handbook, (1979).
Dear, *Intrascience Chemistry Reports*, vol. 5, No. 1, 37 (1971).

*Primary Examiner*—Natalie Trousof
*Assistant Examiner*—L. Hendriksen
*Attorney, Agent, or Firm*—Donald M. Sell; James A. Smith; Lorraine R. Sherman

[57] ABSTRACT

Polymerizable monomer compounds selected from the group having the formulae:

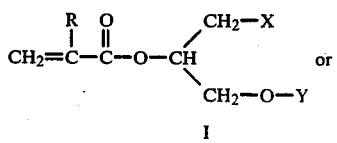

or

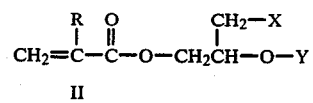

wherein
R is hydrogen or methyl;
X is fluoro, chloro, bromo, iodo, hydroxyl, perfluoroalkylsulfonoxy of one to three carbon atoms, perfluoroacyloxy of one to three carbon atoms, benzoyloxy, or trichloroacetoxy;
Y is trichloroacetyl, perfluoroacyl of the formula

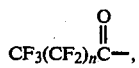

trialkylsilyl of the formula $[CH_3(CH_2)_m]_3Si-$ or hydrogen, wherein n is zero to six; and m is zero to three, with the proviso that when Y in Formula I or II is hydrogen, X is selected from fluoro, chloro, bromo, iodo in Formulas I and II, and additionally from hydroxyl in Formula I, are disclosed. Polymers and copolymers of the invention are useful for preparing hydrogel processed articles such as contact lenses, and when dissolved in solvents they can be coated onto articles and then hydrolyzed to provide hydrogel coatings.

12 Claims, No Drawings

ACRYLATE AND METHACRYLATE MONOMERS AND POLYMERS

TECHNICAL FIELD

The present invention relates to novel acrylate and methacrylate ester monomers and homopolymers and copolymers thereof. In another aspect, it relates to a process for preparing the monomers of the invention. The polymers and copolymers of the invention are useful for preparing hydrogel processed articles such as contact lenses, and when dissolved in solvents they can be coated onto articles and then hydrolyzed to provide hydrogel coatings.

BACKGROUND ART

Certain substituted propyl acrylate and methacrylate esters are known in the art. U.S. Pat. No. 4,192,685 describes compounds which have the formula $$CH_2=\overset{R^1}{\underset{|}{C}}-COO+(CH_2)_p(CHR^2)_q(CH_2)_r-O\overline{+_n}R^3$$

wherein n is an integer of at least 1, p, q, and r are 0 or an integer of at least 1 with the proviso that p+q+r equals 2–6, $R^1$ is a hydrogen or a methyl group, $R^2$ is a lower alkyl group optionally substituted with a halogen atom, and $R^3$ is an alkyl, aryl or acyl group optionally having a substituent. These compounds are said to be useful in photocurable resin compositions.

It is known in the art to esterify hydroxyl groups bonded to alkyl groups of both hydroxyalkyl acrylates and methacrylates. U.S. Pat. No. 3,470,124 describes monomers of the formula R'COO—Y—OOCR", wherein R'COO is a perfluoroalkanoic acid residue; R"COO is a residue of a polymerizable alkenoic acid; and Y is a residue of an organic compound selected from the group consisting of aliphatic, aliphatic-aromatic and aromatic dihydric alcohols as well as the functional derivatives thereof. The functional derivatives refer to the precursors of the dihydric alcohols. No functional derivatives of Y are listed or shown in the examples. Only methyl derivatives are exemplified. No derivatives which include halogen or ester derivatives of the Y moiety of the monomers are mentioned. These monomers are prepared by usual esterification methods known in the art and are oleophobic viscous oils and are useful in treating fibers, paper, wool, brick, etc. to make them oil-resistant.

British Pat. No. 1,118,007 describes hydroxyalkyl(-meth)acrylate esters of perfluoroalkanoic acids and their polymers. They claim monomers which provide polymers with at least three perfluorinated carbon atoms which possess hydrophobic and oleophobic properties and are useful for coating materials and sizing cloth to give resistance to soiling. U.S. Pat. No. 3,459,722 describes the reaction of hydroxyethyl methacrylate with 2-(perfluoro-n(or iso)-propoxy)perfluoropropionyl fluoride to provide the expected ester, 2-(perfluoro-n(or iso)propoxy)perfluoropropionoxyethyl methacrylate, which is useful for treating fabrics and yarns to render them repellant to oil and water. U.S. Pat. No. 3,595,944 describes polymers containing 2H,2-perfluoropropyl acrylate, which provide oil- and water-repellant compositions.

Reactions of trifluoroacetic anhydride are described in Dear, *Intrascience Chemistry Reports*, Vol. 5, No. 1, 37 (1971). It is reported there (page 45) that: "Derivatives of acrylic and methacrylic acid have been polymerized by heating with a mixture of trifluoroacetic anhydride and an amine oxide". No reactions of trifluoroacetic anhydride with epoxides are reported.

SUMMARY OF THE INVENTION

Briefly, this invention provides readily solvolyzable, polymerizable novel acrylate and methacrylate monomers and polymers thereof and a process for their preparation. The monomers are represented by the formulae:

$$CH_2=\overset{R}{\underset{|}{C}}-\overset{O}{\overset{\|}{C}}-O-CH\overset{CH_2X}{\underset{CH_2O-Y}{<}} \qquad \text{Formula I}$$

$$CH_2=\overset{R}{\underset{|}{C}}-\overset{O}{\overset{\|}{C}}-OCH_2\overset{CH_2X}{\underset{|}{CH}}-O-Y \qquad \text{Formula II}$$

wherein
R is hydrogen or methyl;
X is fluoro, chloro, bromo, iodo, hydroxyl, perfluoroalkylsulfonoxy of one to three carbon atoms or perfluoroacyloxy of one to three carbon atoms, benzoyloxy, and trichloroacetoxy;
Y is trichloroacetyl, perfluoroacyl of the formula $$CF_3(CF_2)_n\overset{O}{\overset{\|}{C}}-, \qquad \text{Formula III}$$

trialkylsilyl of the formula $$[CH_3(CH_2)_m]_3Si-,$$

Formula IV or hydrogen, wherein n is zero to six; m is zero to three; and with the proviso that when Y is hydrogen in Formula I or II, X is selected from fluoro, chloro, bromo, and iodo in Formulas I and II, and additionally in Formula I, X can be hydroxyl.

Preferred compounds of the invention are those wherein the perfluoroacyl and perfluoroacyloxy groups contain two carbon atoms.

It is not believed that it has been previously known in the art that an electrophilic reagent such as trifluoroacetic anhydride will react with glycidyl acrylate and methacrylate as shown in this invention. This novel reaction is surprising in view of the fact that Applicant has found that acetic anhydride will not react appreciably (if at all) in an analogous fashion even in the presence of acid catalyst. It is further surprising that in the process of the invention when reagents such as trifluoroacetic anhydride react with glycidyl acrylate and methacrylate, the acrylate or methacrylate functionality may rearrange to the 2-position of the glycidyl group. Under some conditions up to 100 percent of the rearranged product is formed.

By reason of the unsaturation of the monomers of the invention they are capable of forming homopolymers as well as copolymers with each other and with other monomers copolymerizable therewith such as (a) with acrylates or methacrylates such as ethoxyethyl acrylate or methacrylate, methyl(meth)acrylate, glycidyl(meth)acrylate, butyl(meth)acrylate; and di(meth)acrylates such as ethylene glycol di(meth)acrylate, polyethylene glycol di(meth)acrylate, methoxy poly(ethylene glycol)mono(meth)acrylate, and the like; (b) with styrenes such as styrene, alpha-methylstyrene, and p-chlorostyrene; (c) with acrylamides and methacrylamides such as acrylamide, dimethylacrylamide, isopropylacrylamide, and phenylacrylamide; (d) with ethylenically-unsaturated monomers such as vinyl chloride, vinyl acetate, and vinylidene fluoride, and (e) with allyl derivatives, such as diallyl phthalate, triallyl cyanurate, and the like.

Copolymers can be formed from the monomers of the present invention and any compatible ethylenically-unsaturated monomer in any proportion. Preferably, the copolymer contains at least 5 percent by weight of at least one monomer of the invention and most preferably at least 50 percent by weight of a monomer of the invention.

Homopolymers of the invention include units having the following formulae:

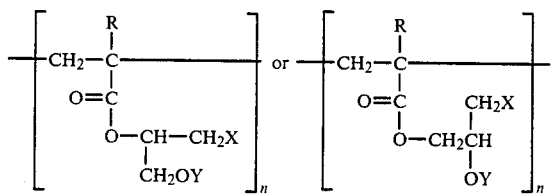

wherein R, X, and Y are as defined above, and n has a value of 200 to 2000, preferably 300 to 1200, to provide the polymers with approximate molecular weights in the range of 100,000 to 1,000,000, preferably 100,000 to 400,000.

When the monomers of the invention form copolymers, units selected from the above structures and comonomer units may react in any proportion and will be distributed throughout the polymer in more or less random fashion depending upon the comonomer and the degree of its similarity of polymerization kinetics to the monomer of Formula I or II, as is known to those skilled in the art.

The invention provides a novel synthetic process whereby the novel monomers of the invention are obtained. In this process, preferably glycidyl acrylate or glycidyl methacrylate is reacted under mild conditions (e.g., 15° to 30° C.) with an electrophilic reagent to provide a novel substituted normal-propyl or isopropyl acrylate or methacrylate of Formulae I (rearranged product) and II. In order to obtain monomers of the invention wherein X and/or —OY is hydroxy, the monomer is obtained by hydrolysis of compounds wherein X is perfluoroalkylsulfonoxy or perfluoroacyloxy and/or —OY is as defined hereinabove. These monomers, i.e., those wherein X and/or —OY is hydroxy, constitute a preferred subclass of the invention.

As used in this application:

"solvolyzable" means an ester linking group capable of cleaving into a carboxyl-containing compound (e.g., amide, ester, or acid) and an alcohol in the presence of a nucleophile such as water or a weak base such as ammonia or an organic amine (at room temperature) or in the presence of a lower ($C_1$ to $C_4$) alkanol (at temperatures up to 60° C.).

"hydrogel" means a material which absorbs a large percentage of water, i.e., in the range of 10 to 95 percent by weight, without itself dissolving in water;

"prehydrogel" means a polymer that can be solvolyzed to give a hydrogel;

"thermally processable (thermoprocessable) polymer" means a polymer which may be heated to a temperature in the range of 200° to 400° F., and preferably at about 300° F., and then cooled to provide a shaped article which will thereafter retain its shape under normal temperatures; and "solvent-coatable polymer" means a polymer which may be dissolved in a suitable solvent, which resulting solution may then be poured onto or over an article to be coated, and the solvent evaporated to provide the coated article. For some purposes, i.e. to obtain a hydrogel coating, the coating may be hydrolyzed, e.g., by heating in aqueous base, then the coated article is washed to provide the desired hydrogel coating.

DETAILED DESCRIPTION

Preparation of the novel monomers of the invention proceeds according to Equation I, which is carried out under mild to moderate conditions, the reactants being present in equimolar amounts, as follows:

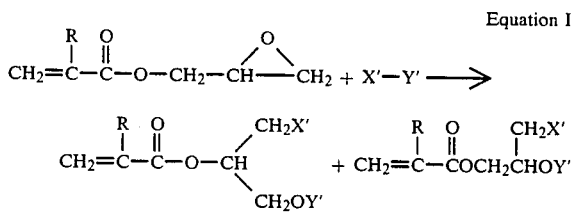

Equation I wherein

R is hydrogen or methyl;

X' is fluoro, chloro, bromo, iodo, perfluoroalkylsulfonoxy of one to three carbon atoms or perfluoroacyloxy of one to three carbon atoms, benzoyloxy, and trichloroacetoxy;

Y' is trichloroacetyl or perfluoracyl of the formula

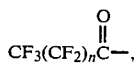

III trialkylsilyl of the formula

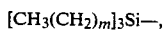

IV wherein n is zero to six; m is zero to three.

In the process of the invention, the compound X'—Y' cannot contain a hydroxyl group. The process is preferably carried out in a solvent which is inert under the reaction conditions, i.e., a non-hydroxylic solvent. Halogenated alkanes, e.g., dichloromethane, chloroform, dichloroethane, carbon tetrachloride, and the like, are suitable solvents. Other suitable non-hydroxylic solvents include acetonitrile (a preferred solvent), tetrahydrofuran, toluene, ethyl acetate, acetone, methyl ethyl ketone, and the like.

The temperatures required are quite mild. For many purposes, temperatures of 15° to 30° C. are adequate. Higher temperatures (e.g., up to 90° C.) may be used to increase the rate of reaction.

The preferred electrophilic agent is trifluoroacetic anhydride. Other suitable electrophilic agents include benzoyl trifluoroacetate, trichloroacetic anhydride, trichloroacetyl chloride, and trifluoroacetyl chloride. When the electrophilic reagent in Equation I is not trifluoroacetic anhydride, the product is generally a mixture of products of Formula I and Formula II. When trifluoroacetic anhydride is used greater than 90 percent by weight of the compound of Formula I (the rearranged product) is obtained.

Preferably the reacting monomer is glycidyl acrylate or glycidyl methacrylate. It has been found that an ester group separated from the epoxide group by an alkylene chain having 1 to 3 carbon atoms, and preferably a methylene group, is present in the reactants useful in the process of the invention. For example, the following epoxides do not react with trifluoroacetic anhydride:

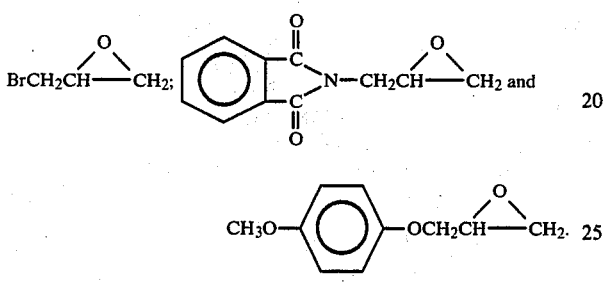

It is anticipated that epoxides of the formula

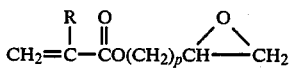

wherein p is 2 to 4, will react in the process of the invention to provide compounds having the formulae:

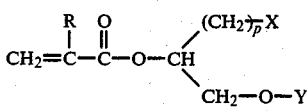

or

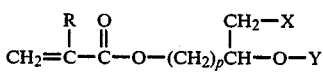

wherein R, X and Y are as defined above.

Minor amounts, i.e. 0.01 to 1.0 weight percent of acid, i.e., inorganic acid such as hydrochloric acid, or organic acid, such as trifluoroacetic acid or para-toluenesulfonic acid, may be used if necessary to catalyze the reaction in the process of the invention.

It is preferable to carry out the process of the invention under dry, i.e., non-aqueous, conditions to avoid side reactions of the monomeric starting materials and products. It may also be desirable to carry out the synthetic process of the invention in the presence of a free-radical scavenger, i.e., a polymerization inhibitor such as 4-methoxyphenol present in an amount in the range of 0.01 to 1.0 weight percent.

In order to prepare monomers of the invention wherein X and/or —OY is hydroxy, it is preferred to solvolyze the perhaloacyloxy and/or perfluoroalkylsulfonoxy groups of the selected monomers of Formulae I or II in a non-aqueous environment, for example, in the presence of an anhydrous $C_1$ to $C_4$ alcohol, such as methanol or ethanol. However, these solvolysis reactions may also be carried out in water alone, in water in the presence of a weak base, or in a mixture of water and a water-miscible solvent such as an alcohol as well as ammonia in an alcohol solvent.

Presently preferred monomers of the invention are those wherein, in Formulae I and II, R is methyl, Y is trifluoroacetyl and X is chloro, fluoro or trifluoroacetoxy. Another preferred subclass of monomers of the invention is that wherein Y is trimethylsilyl and X is fluoro, chloro or trifluoroalkylsulfonoxy. A third preferred subclass consists of compounds wherein n of Formula III is zero. Another preferred subclass is compounds wherein m of Formula IV is zero.

Another preferred subclass of monomers is obtained by solvolysis of monomers wherein R is hydrogen or methyl, X is halogen, benzoyloxy, perfluoroalkylsulfonoxy or perfluoroacyloxy, and Y is trichloroacetyl, perfluoroacyl or trialkylsilyl to provide monomers of the formulae:

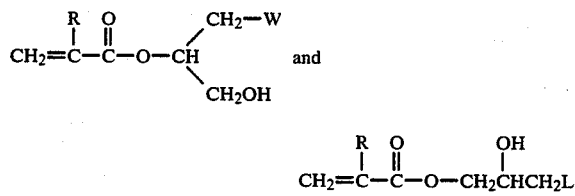

wherein W is halogen or hydroxy, and L is halogen.

Novel and useful polymers of the invention are obtained by polymerization of the monomers of Formulae I and II to form homopolymers, copolymers with each other, and copolymers with compatible copolymerizable monomers. The polymerization of the monomers may be carried out by employing initiators which generate free-radicals on application of activating energy as is conventionally used in the polymerization of ethylenically unsaturated monomers. Included among useful free-radical initiators are the thermally activated initiators such as organic peroxides, organic hydroperoxides, and azo compounds. Representative examples of such initiators include benzoyl peroxide, tertiary-butyl perbenzoate, diisopropyl peroxydicarbonate, cumene hydroperoxide, azobis(isobutyronitrile), and the like. Generally, from about 0.1 to 5 percent by weight of thermal initiator is used.

Photoinitiators may also be employed to initiate polymerization. Such initiators are well known and have been described in the polymerization art, e.g., Chapter II of "Photochemistry" by Calvert and Pitts, John Wiley and Sons (1966). The preferred photoinitiators facilitate polymerization when the composition is irradiated. Representative examples of such initiators include acyloin and derivatives thereof, such as benzoin, benzoin methyl ether, benzoin ethyl ether, benzoin isopropyl ether, benzoin isobutyl ether and α-methylbenzoin; diketones such as benzil and diacetyl, etc.; ketones such as acetophenone, α,α,α-trichloroacetophenone, α,α,α-tribromoacetophenone, α,α-diethoxyacetophenone (DEAP), methyl benzoylformate, 2-hydroxy-2-methyl-1-phenyl-1-propanone, o-nitro-α,α,α-tribromoacetophenone, benzophenone and p,p'-tetramethyldiaminobenzophenone; α-acyloxime esters such as benzil-(O-ethoxycarbonyl)-α-monoxime; ketone/amine combinations such as benzophenone/N-methyldiethanolamine, benzophenone/tributylamine and benzophenone/Michler's ketone; and benzilketals such as benzildimethylketal, benzildiethylketal and 2,5-dichlorobenzildimethylketal. Normally, the photoinitiator is used in amounts ranging from about 0.01 to 5 percent by weight of the total monomeric composition. When the quantity is less than 0.01 percent by weight, the photopolymerization rate becomes extremely low. If the photoinitiator is used in excess of 5 percent by weight, no correspondingly improved effect is observed. Preferably, about 0.05 to 1.0 percent of photoinitiator is used in the polymerizable compositions.

Polymerization may be carried out in bulk in a conventional manner. When the activating energy is ultraviolet light, the irradiation is typically carried out at a temperature in the range of 0° to 50° C. for 0.5 minute to 5 hours or more. Following ultraviolet irradiation, the composition may be heated at 50° to 100° C. to complete the polymerization.

When the activating energy is only heat, polymerization is usually carried out at a temperature in the range of 40° to 140° C. for about 5 to 50 hours. The polymerization can also be carried out in stages. Thus, in a first stage, the composition may be heated at 40° to 60° C. for about 5 to 25 hours, and in a second stage it may be heated at 50° to 100° C. for 5 to 25 hours. It is to be understood, of course, that the polymerization conditions are not limited to such temperature and time conditions nor to the use of ultraviolet radiation or heat as the initiating energy.

Copolymers are preferably prepared by mixing compatible monomers with the monomers of the invention in the presence of free-radical catalysts in the presence of heat or UV irradiation as necessary to obtain the desired reaction rate.

When neither X nor —OY is hydroxy (i.e., X is X' and Y is Y') in the monomers of the invention, a novel subclass of thermoprocessable or solvent coatable polymers and copolymers is obtained. It is possible to react these polymers and copolymers either before or after they are thermoprocessed or solvent-coated. The reaction which is carried out on the thermoprocessable polymers and copolymers renders them non-thermoprocessable. This reaction is solvolysis of the perhaloacyloxy or perfluoroalkylsulfonoxy groups to provide hydroxy-terminated side chains. This solvolysis is carried out under relatively mild conditions (at temperatures up to 60° C.), e.g., in the presence of sodium bicarbonate or ammonium hydroxide or by use of methanol or water alone. Homopolymers and copolymers with hydroxy-terminated side chains are not thermally processable but provide relatively tough hydrogel polymers, i.e., they absorb up to about 10 to 95 weight percent of water. Thermal processing and solvolysis can provide articles with improved water absorption and in some instances improved strength even when compared to heavily cross-linked polymers. The present process avoids both of the factors which can prevent thermal processability, i.e., hydrogen bonding by hydroxyl functional groups and cross-linking.

For some purposes, it is desired to thermally process or solvent-coat the polymers and copolymers of the invention wherein neither X nor —OY is hydroxy, to obtain processed articles, then to solvolyze the groups on the side chains to hydroxy groups. The resulting processed articles are then hydrogels and may be suitable, e.g., for contact lenses. Additionally, the polymers, soluble in suitable solvents, such as ethyl acetate and tetrahydrofuran, can be coated onto articles and then solvolyzed to give hydrogel coatings.

There are various ways to prepare shaped articles from polymers and copolymers of the invention. For example, the article may be prepared by thermoprocessing or solvent coating the polymers and copolymers of the invention; the article may be prepared by polymerizing in a container which has the shape desired for the polymeric product, e.g., a film, a sheet, or an intraocular or a contact lens. Polymerized material may also be directly machined or shaped after polymerization. In some cases, the polymers will be solvolyzed and hydrated to form useful articles.

In other cases, the resulting polymer will be used as is, for example, as a film or sheet. The polymers obtained may be cross-linked by conventional cross-linking agents, such as bis(methacryloxy)ethane, to provide hard, infusible, transparent polymers.

When neither X nor —OY is hydroxy in the monomer, the polymer obtained is a typical (meth)acrylate polymer which is transparent, thermally processable and has a glass transition temperature in the range of 0° to 60° C. They are typically used as prehydrogels for various articles or hydrophilic coatings (i.e., materials with non-fogging surfaces).

Objects and advantages of this invention are further illustrated by the following examples, but the particular materials and amounts thereof recited in these examples, as well as other conditions and details, should not be construed to unduly limit this invention.

EXAMPLE 1—monomer preparation

To a solution of 3.6 g (20 mmole) of trichloroacetyl chloride in 25 ml of tetrahydrofuran was added dropwise 2.8 g (20 mmole) of glycidyl methacrylate. The solution was heated at reflux for three hours then stirred at about 20° C. for about 60 hours. The solvent and volatile by-products were removed by evaporation under vacuum. Nuclear magnetic resonance spectral analysis confirmed the conversion of the starting materials to the product, 1-chloro-3-(trichloroacetoxy)propyl-2-methacrylate,

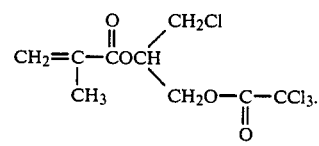

EXAMPLE 2—monomer preparation

Into a cold solutin (ice bath temperature) of 7.1 g (50 mmole) of glycidyl methacrylate in 100 ml of dichloromethane was bubbled 6.0 g (45 mmole) of trifluoroacetyl chloride. The solution was allowed to stand at about 20° C. for 16 hours then evaporated to remove low boiling components. The residue was distilled in vacuo after the addition of 0.5 g methylene blue. Fractions boiling between 53° and 60° C. at 0.4 mm of Hg were analyzed by gas-liquid phase chromatography to show a single major component obtained in 35 percent yield. Infrared and nuclear magnetic resonance analyses confirmed the product to be 1-chloro-3-(trifluoroacetoxy)-propyl-2-methacrylate,

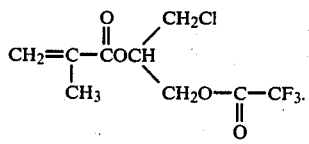

EXAMPLE 3—monomer preparation

To a cold solution (0° C.) of 25 g (120 mmole) of trifluoroacetic anhydride and 2 drops of trifluoroacetic acid in 100 ml of dichloromethane was added dropwise 14.2 g (100 mmole) of glycidyl methacrylate. The mixture was then allowed to warm to about 20° C. and stirred for 20 hours. The solvent was removed by evaporation and the residue was distilled in vacuo to provide 1,3-bis(trifluoroacetoxy)propyl-2-methacrylate, b.p. 85° C./0.2 mm of Hg. Infrared and nuclear magnetic resonance spectral analyses confirmed that the product was 100 percent of the isomer (in a yield of 80 percent) having the structural assignment as

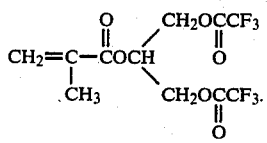

EXAMPLE 4—monomer preparation
(alternative method to EXAMPLE 3)

To a cold (0° C.) solution of 150 g (0.72 mmole) of trifluoroacetic anhydride in 500 ml of dichloromethane was added dropwise 85.2 g (0.6 mmole) of glycidyl methacrylate. The reaction mixture was then stirred at about 20° C. for about 16 hours. The mixture was evaporated in vacuo to remove the dichloromethane, 4 g of methylene blue was added, and the residue was vacuum distilled. The fractions boiling from 65° to 75° C. at 0.25 mm of Hg were chiefly (greater than 93 percent by gas-liquid chromatographic analysis) 1,3-bis(trifluoroacetoxy)propyl-2-methacrylate (see EXAMPLE 3 for structure) according to nuclear magnetic resonance spectral analysis.

EXAMPLE 5—monomer preparation

To a stirred solution of 20.4 g of 1,3-bis(trifluoroacetoxy)propyl-2-methacrylate in 100 ml of methanol was added 8 mg of 4-methoxyphenol. After one hour the methanol was removed by evaporation and 100 ml of fresh methanol was added. The solution was stirred at about 20° C. for 14 hours. The methanol was then removed by evaporation and 100 ml of fresh methanol was added. After 48 hours the methanol was again evaporated and fresh methanol was added. After five additional hours the methanol was evaporated. Nuclear magnetic resonance and infrared spectral analyses of the product confirmed it to be 1,3-bis(hydroxy)propyl-2-methacrylate,

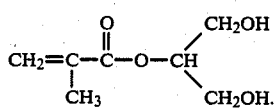

EXAMPLE 6—monomer preparation

To a cold (−10° C.) solution of 1.0 g (4.9 mmole) of iodotrimethylsilane in 7 ml of dichloromethane was added dropwise 0.70 g (4.9 mmole) of glycidyl methacrylate. The reaction was cooled while stirring for four hours. The solvent was removed in vacuo and the reaction product analyzed by infrared and nuclear magnetic resonance spectral analyses. The desired product, 1-iodo-3-(trimethylsilyloxy)propyl-2-methacrylate,

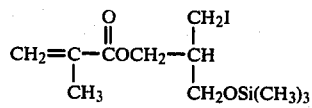

was 21 percent of the product. The unrearranged product, 3-iodo-2-(trimethylsilyloxy)propyl-1-methacrylate,

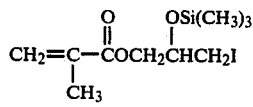

was 79 percent of the product obtained.

EXAMPLE 7—monomer preparation

To a stirred solution of 0.6125 g (2.75 mmole) of trimethylsilyl trifluoromethanesulfonate in 5 ml dichloromethane was added dropwise 0.4 g of glycidyl methacrylate. The reaction was exothermic and it was cooled by an ice bath and stirred for 16 hours. The solvent was removed in vacuo and the product analyzed by a nuclear magnetic resonance spectrum. The analysis showed that a mixture of 1-trifluoromethylsulfonoxy-3-(trimethylsilyloxy)propyl-2-methacrylate,

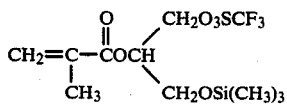

and 2-trimethylsilyloxy-3-(trifluoromethylsulfonoxy)-propyl-1-methacrylate,

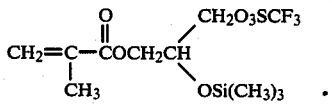

was obtained.

EXAMPLE 8—monomer preparation

Into a cold solution (0° C.) of 5 g (3.9 mmole) of glycidyl acrylate under nitrogen in 100 ml of dichloromethane was slowly added 12.6 g (23.8 mmole) of trifluoroacetic anhydride. The solution was stirred at about 20° C. for 16 hours and it was then evaporated to remove low boiling components. The residue was distilled in vacuo after the addition of 0.2 g methylene blue. Fractions boiling between 75° and 80° C. at 0.8 mm of Hg were collected. Infrared and nuclear magnetic resonance analyses confirmed the product to be 1,3-bis(trifluoroacetoxy)propyl-2-acrylate, $$CH_2=CH-\overset{O}{\overset{\|}{C}}OC\overset{CH_2OOCCF_3}{\underset{CH_2OOCCF_3}{H}}$$

EXAMPLE 9—monomer preparation

To 4.3 g (10 mmole) of perfluoro-n-octanoyl chloride in 25 ml of acetonitrile was added 1.4 g (10 mmole) of glycidyl methacrylate. The solution was stirred at about 20° C. for 16 hours. Evaporation of the solvent provided 5.5 g of a mixture of 1-chloro-3-(perfluoro-n-octanoyloxy)propyl-2-methacrylate, $$CH_2=\underset{CH_3}{\overset{\|}{C}}-\overset{O}{\overset{\|}{C}}OC\overset{CH_2Cl}{\underset{CH_2OOCC_7F_{15}}{H}}$$

and 1-chloro-2-(perfluoro-n-octanoyloxy)propyl-3-methacrylate, $$CH_2=\underset{CH_3}{\overset{\|}{C}}-\overset{O}{\overset{\|}{C}}OCH_2C\overset{CH_2Cl}{\underset{O_2CC_7F_{15}}{H}}$$

in a ratio of 1 to 3, respectively. The structures were confirmed by infrared and nuclear magnetic resonance spectral analyses.

EXAMPLE 10 alternative preparation for EXAMPLE 9 monomers

Using the procedure and quantities of reactants of EXAMPLE 9 and changing the solvent to carbon tetrachloride inhibited by 3 mg of methoxyhydroquinone, the reactants were heated at reflux for 5 hours. Evaporation of the reaction mixture provided 5.4 g of an oil which was a mixture of the same two products which were obtained in EXAMPLE 9, i.e., 1-chloro-3-(perfluoro-n-octanoyloxy)propyl-2-methacrylate and 1-chloro-2-(perfluoro-n-octanoyloxy)propyl-3-methacrylate in a ratio of 1 to 2, respectively. The structures were again confirmed by infrared and nuclear magnetic resonance spectral analysis.

EXAMPLE 11—monomer preparation

To a solution of 1.4 g (10 mmole) of glycidyl methacrylate in 25 ml of acetonitrile was added 6 g (10 mmole) of trichloroacetic anhydride. The solution was stirred at 20° C. for sixteen hours. Removal of the solvent provided an oil which was confirmed by nuclear magnetic resonance spectral analysis as 1,3-bis(trichloroacetoxy)-propyl-2-methacrylate, $$CH_2=\underset{CH_3}{\overset{\|}{C}}-\overset{O}{\overset{\|}{C}}OC\overset{CH_2OOCCCl_3}{\underset{CH_2OOCCCl_3}{H}}$$

EXAMPLE 12—monomer preparation

A mixture of glycidyl methacrylate (1.4 g), benzoyl trifluoroacetate, (2.2 g) and 25 cc of acetonitrile was heated at 78° C. for 16 hours. The solvent was removed on a rotary evaporator and analysis was carried out by gas chromatography/mass spectrometry and nuclear magnetic resonance spectroscopy. Methacrylates in the product mixture were confirmed as glycidyl methacrylate, 1,3-bis(trifluoroacetoxy)propyl-2-methacrylate, $$CH_2=\underset{CH_3}{\overset{\|}{C}}-\overset{O}{\overset{\|}{C}}OC\overset{CH_2OOCCF_3}{\underset{CH_2OOCCF_3}{H}}$$

and 1-benzoyloxy-3-(trifluoroacetoxy)propyl-2-methacrylate, $$CH_2=\underset{CH_3}{\overset{\|}{C}}-\overset{O}{\overset{\|}{C}}OC\overset{CH_2OOCC_6H_5}{\underset{CH_2OOCCF_3}{H}}$$

in a ratio of 3 to 1 to 3, respectively.

EXAMPLE 13—article preparation

A mixture of 12 g of 1,3-bis(trifluoroacetoxy)propyl-2-methacrylate, prepared as in EXAMPLE 3, 1.5 g of methyl methacrylate, 1.5 g of ethoxyethyl methacrylate and 17 mg diisopropyl percarbonate was degassed with nitrogen. A film cell consisting of two glass plates separated by a washer-like spacer of poly(tetrafluoroethylene) of about 305 micrometers was filled with this solution and the mixture was cured at 60° C. for 4.75 hours. The resulting film was placed in 1M aqueous ammonium hydroxide solution and stirred for 26.5 hours. The film was then rinsed three times with distilled water and mixed in 0.9 percent aqueous sodium chloride solution for 18 hours. The percent by weight hydration of the film was determined to be 40.6.

EXAMPLE 14 thermoprocessing to prepare a contact lens

To a mixture of 3.6 g of ethoxyethyl methacrylate and 14.4 g of 1,3-bis(trifluoroacetoxy)propyl-2-methacrylate (prepared in EXAMPLE 3) was added 20 mg of diisopropyl percarbonate. The solution was degassed with nitrogen and poured into a polymerization cell. Thermal polymerization was carried out at 65° C. for 14 hours. The resulting polymer was thermoformed into a lens at 149° C. (300° F.). The lens was placed in stirred 1M ammonium hydroxide for for 24 hours, then rinsed in distilled water for 24 hours, to provide a hydrated lens with a water content of 42 weight percent.

EXAMPLE 15 thermoprocessing to prepare a contact lens

To a mixture of 3.6 g of methyl methacrylate and 14.4 g of 1,3-bis(trifluoroacetoxy)propyl-2-methacrylate (prepared as in EXAMPLE 3) was added 20 mg of diisopropyl percarbonate. Nitrogen was bubbled through the solution for 30 minutes. The solution was polymerized by heating at 60° C. for 4 hours in a Teflon ® container 1.26 mm in thickness. The resulting polymer was pressed at 149° C. (300° F.) for 10 minutes in a contact lens mold made of metal. The lens was placed in a stirred 1M ammonium hydroxide solution for about 16 hours then rinsed with distilled water. The lens remained transparent and retained its shape after hydration.

EXAMPLE 16—thermoprocessing

To a mixture of 3.6 g of ethoxyethyl acrylate and 14.4 g of 1,3-bis(trifluoroacetoxy)propyl-2-methacrylate (prepared as in EXAMPLE 3) was added 20 mg of diisopropyl percarbonate. The mixture was degassed by bubbling through nitrogen gas. The monomer solution was placed in a mold and polymerized at 65° C. for 17 hours. The polymer was heated to 149°–185° C. (300°–400° F.), but it did not thermoform. It was then hydrolyzed by heating in 1M ammonium hydroxide solution to form a clear polymer. This polymer was placed in distilled water for about 16 hours to provide a hydrated polymer. The weight percent hydration was 63.6.

EXAMPLE 17—article preparation

To 10 g of 1,3-bis(trifluoroacetoxy)propyl-2-methacrylate (prepared as in EXAMPLE 3) was added about 30 mg of diisopropyl percarbonate. Nitrogen was bubbled through the solution. After 20 minutes the solution was injected into a film cavity with a 40 mil thick Teflon TM spacer. This container was placed in a 78° C. oven for 3.5 hours. The polymer film was then immersed in water on a steam bath for 22.5 hours. The water content was determined to be 82 weight percent.

EXAMPLE 18

This example illustrates the specialized nature of the process of the invention, i.e., reactants of the formula $X-Y^2$, i.e., compounds wherein X is chlorine or bromine as defined hereinabove and $Y^2$ is

wherein $R_2$ is listed below, do not give high yields of rearranged product (Formula I) for most reactants. As noted in Example 2, when $R_2$ was $CF_3$, the only product presented in sufficient quantity to be isolated was the rearranged product.

Glycidyl methacrylate (GMA), 30 mmoles, an appropriate acyl halide, 30 mmoles, and 30 cc of acetonitrile were mixed together, heated and stirred for varying times depending on the acyl halide. The solvent was removed leaving the product as an oil. The following TABLE lists the various reagents, products and conditions.

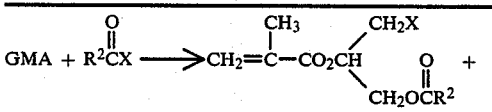

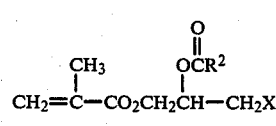

| $R_2$ | X | percent II | percent I | CONDITIONS |
|---|---|---|---|---|
| $CCl_3$ | Cl | 93 | 7 | 3 hrs. room temperature. |
| $CHCl_2$ | Cl | greater | less | 18 hrs. room temperature. |

-continued

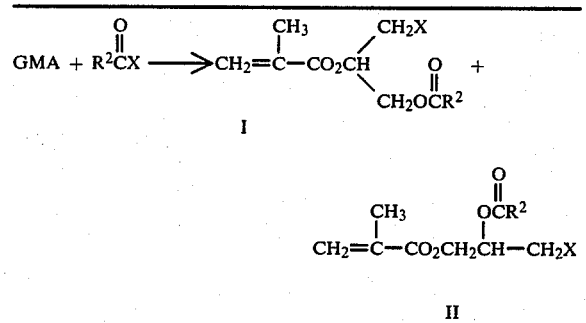

| $R_2$ | X | percent II | percent I | CONDITIONS |
|---|---|---|---|---|
| | | than 97 | than 3 | |
| $CH_2Cl$ | Cl | 83 | 17 | 24 hrs. at 50° C. |
| $CH_3$ | Cl | 92 | 8 | 20 hrs. at 70° C. |
| $CH_3$ | Br | 100 | not detected | 24 hrs. at 70° C. |
| $CH_3CH_2$ | Cl | 100 | not detected | 20 hrs. at 70° C. |

Various modifications and alterations of this invention will become apparent to those skilled in the art without departing from the scope and spirit of this invention, and it should be understood that this invention is not to be unduly limited to the illustrative embodiments set forth herein.

I claim:

1. A monomer having the formulae:

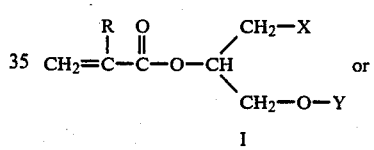

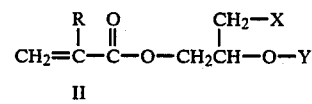

wherein
R is hydrogen or methyl;
X is fluoro, chloro, bromo, iodo, perfluoroalkylsulfonoxy of one to three carbon atoms, perfluoroacyloxy of one to three carbon atoms, benzoyloxy, or trichloroacetoxy;
Y is trichloroacetyl, perfluoroacyl of the formula

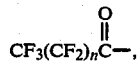

or trialkylsilyl of the formula $[CH_3(CH_2)_m]_3Si-$ wherein n is zero to six; and m is zero to three.

2. The monomer

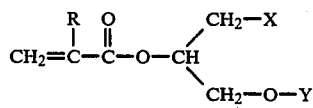

according to claim 1.

3. The monomer

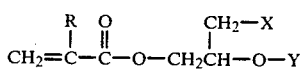

according to claim 1.

4. The monomer according to claim 1 wherein R is methyl.

5. The monomer according to claim 1 wherein
R is hydrogen or methyl,
X is fluoro, chloro, bromo, iodo, benzoyloxy, perfluoroalkylsulfonoxy or perfluoroacyloxy, and
Y is trichloroacetyl, perfluoroacyl or trialkylsilyl.

6. A monomer having the formulae:

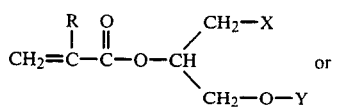

wherein
R is hydrogen or methyl;
X is fluoro, chloro, or trifluoroacetoxy; and
Y is trifluoroacetyl.

7. A monomer having the formulae:

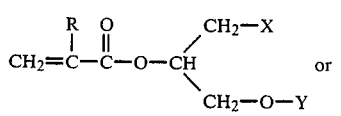

wherein
R is hydrogen or methyl,
X is a group selected from fluoro, chloro, or trifluoroalkylsulfonoxy of one to three carbon atoms, and
Y is trimethylsilyl.

8. A monomer having the formulae:

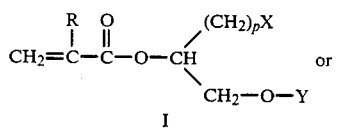

wherein
R is hydrogen or methyl;
X is fluoro, chloro, bromo, iodo, perfluoroalkylsulfonoxy of one to three carbon atoms, perfluoroacyloxy of one to three carbon atoms, benzoyloxy, or trichloroacetoxy;
Y is trichloroacetyl, perfluoroacyl of the formula

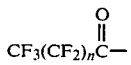

or trialkylsilyl of the formula [CH$_3$(CH$_2$)$_m$]$_3$Si— wherein p is two to four; n is zero to six; and m is zero to three.

9. A monomer having the formulae:

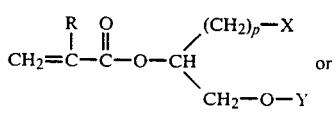

wherein
R is hydrogen or methyl;
X is fluoro, chloro, bromo, iodo, perfluoroalkylsulfonoxy of one to three carbon atoms, perfluoroacyloxy of one to three carbon atoms, benzoyloxy, or trichloroacetoxy;
Y is trichloroacetyl, perfluoroacyl of the formula

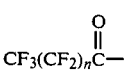

or trialkylsilyl of the formula [CH$_3$(CH$_2$)$_m$]$_3$Si—;
wherein p is one to four; n is zero to six; and m is zero to three, said monomer being the reaction product of an acrylate or methacrylate of the formula

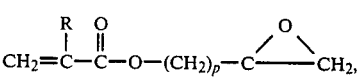

wherein R and p are as previously defined, and an electrophilic reagent so as to provide the monomers as defined above, the reaction being carried out under mild conditions in an inert solvent.

10. A monomer having the formula

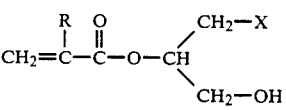

wherein
R is hydrogen or methyl;
X is benzoyloxy or trichloroacetoxy.

11. A monomer having the formula

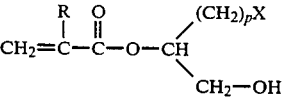

wherein
R is hydrogen or methyl;
X is benzoyloxy or trichloroacetoxy, and
p is two to four.

12. A monomer having the formula:

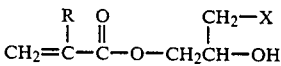

wherein
R is hydrogen or methyl; and
X is benzoyloxy.

* * * * *